United States Patent [19]

Petri, Jr. et al.

[11] Patent Number: 5,665,565

[45] Date of Patent: Sep. 9, 1997

[54] TRANSFECTION OF ENTERIC PARASITES

[75] Inventors: William A. Petri, Jr.; R. Randolph Vines; Jay E. Purdy; Barbara J. Mann, all of Charlottesville, Va.

[73] Assignee: The University of Virginia Patent Foundation, Charlottesville, Va.

[21] Appl. No.: 387,315

[22] Filed: Feb. 13, 1995

Related U.S. Application Data

[63] Continuation-in-part of Ser. No. 273,962, Jul. 12, 1994.

[51] Int. Cl.$^6$ .......................... C12P 21/06; C12N 15/00; C12N 1/20; C07H 21/04
[52] U.S. Cl. .................. 435/69.1; 435/172.3; 435/252.3; 435/320.1; 536/24.1; 935/22; 935/23; 935/33; 935/52; 935/55; 935/56; 935/66
[58] Field of Search .......................... 435/69.1, 172.3, 435/320.1, 252.3; 536/24.1; 935/22, 23, 33, 52, 55, 56, 66

[56] References Cited

PUBLICATIONS

Rose Nickel et al., "Transfection and Transient Expression of Chloramphenicol Acetyltransferase Gene in the Protozoan Parasite *Entamoeba histolytica*", Proc. Natl. Acad. Sci., vol. 91, pp. 7095–7098, Jul. 1994.

Jay E. Purdy et al., "Transient Transfection of the Enteric Parasite *Entamoeba histolytica* and Experssion of Firefly Luciferase", Proc. Natl. Acad. Sci., vol. 91, pp. 7099–7103, Jul. 1994.

Soldati and Boothroyd, "Transient Transfection and Expression in the Obligate Intracellular Parasite *Toxoplasma gondii*", Science 260: 349–352 Apr. 1993.

Furfine and Wang, "Transfection of the *Giardia iamblia* double-stranded RNA virus into *Giardia iamblia* by electroporation of a single-stranded RNA copy of the viral genome", Mol. Cell. Biol. 10(7): 3659–3663 Jul. 1990.

Biorad Life Science Research Products Catalog, pp. 174–176 1993.

Gauss and Lieber, "DEAE–dextran enhances electroporation of mammalian cells", Nucleic Acids Res. 20(24): 6739–40 Dec. 1992.

*Primary Examiner*—Mindy Fleisher
*Assistant Examiner*—Bonnie D. Weiss
*Attorney, Agent, or Firm*—Oblon, Spivak, McClelland, Maier & Neustadt, P.C.

[57] ABSTRACT

The invention provides methods for expressing foreign genes in enteric protozoa. This transfection system was established using a gene ligated to the 5' and 3' flanking DNA regions of a protein-encoding gene from an enteric protozoa. The present invention also provides such transformed enteric protozoa, vaccines produced therefrom and foreign or altered proteins expressed in the same. The ability to introduce and express genes in amebae will now permit both genetic analysis and modification of the virulence of this organism, which remains a serious threat to world health and will facilitate basic research towards the control of this parasite.

26 Claims, 10 Drawing Sheets

BΔ1R8.D3'41   (1000 Bases)    100% ± 7% (9)

(489 Bases)
4B    111% ± 11% (4)

(358 Bases)
4H    142% ± 23% (3)

(287 Bases)
4I    218% ± 61% (4)

(201 Bases)
4F    11% ± 4% (9)

(110 Bases)
6C    0.4% ± 0.2% (4)

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

TAAGAACAAT AATTAAGAGA ATTGAATAAC ATTT       34

( 2 ) INFORMATION FOR SEQ ID NO:2:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

TAACTTTTGG AAATTAAGTT ATTTGTTTT CTTT       34

( 2 ) INFORMATION FOR SEQ ID NO:3:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

TAACTTTTGG AAATTAAGTT ATTTTGTTT CATT       34

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: single ( D ) TOPOLOGY: linear ( x i ) SEQUENCE DESCRIPTION: SEQ ID NO:4:

TAAGCGTTTT AATTTACTTT CTCATTT                                                    27

( 2 ) INFORMATION FOR SEQ ID NO:5:

( i ) SEQUENCE CHARACTERISTICS:
                ( A ) LENGTH: 17 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:5:

TAAGTCATTT TTAGTTT                                                               17

( 2 ) INFORMATION FOR SEQ ID NO:6:

( i ) SEQUENCE CHARACTERISTICS:
                ( A ) LENGTH: 27 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:6:

TAAGTCATAA GTGATTTTTT CATTGAT                                                    27

( 2 ) INFORMATION FOR SEQ ID NO:7:

( i ) SEQUENCE CHARACTERISTICS:
                ( A ) LENGTH: 28 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:7:

TAAACGTTAA TTGAAGATAT TTCATTTT                                                   28

( 2 ) INFORMATION FOR SEQ ID NO:8:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:8:

TAAATGAGTT ATTTGACTTT                                                            20

( 2 ) INFORMATION FOR SEQ ID NO:9:

( i ) SEQUENCE CHARACTERISTICS:
                ( A ) LENGTH: 37 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:9:

TAGAAATAAT TAATAAAATT AATTATTTCT TCTTTCC                                         37

( 2 ) INFORMATION FOR SEQ ID NO:10:

( i ) SEQUENCE CHARACTERISTICS:
                ( A ) LENGTH: 26 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:10:

TAATTAATTT AATTATCTTA TTATTT                                         26

( 2 ) INFORMATION FOR SEQ ID NO:11:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

TGAATATTTC ACAGTTAAAT CACTTCTTTT TATG                                34

( 2 ) INFORMATION FOR SEQ ID NO:12:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

TAAAACAAAC AAGATAATTT AATACAAATT ATTTT                               35

( 2 ) INFORMATION FOR SEQ ID NO:13:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

TAAGTGAAGT TTCACTTTTC CCCTC                                          25

( 2 ) INFORMATION FOR SEQ ID NO:14:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

TAAATTAATT GATCTCTTTG GGTG                                           24

( 2 ) INFORMATION FOR SEQ ID NO:15:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

TAAGTTTTAA GCTACTCAAT TGAGTAAATT TTCATAC                             37

( 2 ) INFORMATION FOR SEQ ID NO:16:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

```
TAACATCCTT TTGTAATTGA TTTTTAACCT TT                                32
```

( 2 ) INFORMATION FOR SEQ ID NO:17:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:17:

```
TGGCCCCGC TGAATTG                                                  17
```

( 2 ) INFORMATION FOR SEQ ID NO:18:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:18:

```
GCGCGCCTCG AGTTTTACAA TTTGGACTT                                    29
```

( 2 ) INFORMATION FOR SEQ ID NO:19:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:19:

```
GCGCGCAAGC TTTTTGATAA GTCATGAGT                                    29
```

( 2 ) INFORMATION FOR SEQ ID NO:20:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:20:

```
GCGCGCGGAT CCCTTTCTAG TTCATTGTC                                    29
```

( 2 ) INFORMATION FOR SEQ ID NO:21:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:21:

```
GCGCGCGAGC TCACGATGTA ACTCAATAA                                    29
```

( 2 ) INFORMATION FOR SEQ ID NO:22:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:22:

```
GCGCGCGGAT CCATAATAAT AATTTCATAT                                   30
```

(2) INFORMATION FOR SEQ ID NO:23:

(i) SEQUENCE CHARACTERISTICS:
       (A) LENGTH: 32 base pairs
       (B) TYPE: nucleic acid
       (C) STRANDEDNESS: single
       (D) TOPOLOGY: linear (xi) SEQUENCE DESCRIPTION: SEQ ID NO:23:

GCGCGCGTCG ACGAACAATA ATTAAGAGAA TT    32

TRANSFECTION OF ENTERIC PARASITES

This application is a continuation-in-part application of U.S. Ser. No. 08/273,962 filed on Jul. 12, 1994.

This invention was made with government support under grants AI26649 and 32615 awarded by the National Institute of Health. The government has certain rights of the invention.

BACKGROUND OF THE INVENTION

1. Field of the Invention

The present invention provides methods for transfecting enteric parasites, transformed enteric parasites and vaccines generated from said transformed enteric parasites.

2. Discussion of the Background

Enteric protozoa cause a variety of diseases in humans. For example, *Entamoeba histolytica* is the cause of amebiasis, a disease which is surpassed only by malaria and schistosomiasis as a parasitic cause of death (Walsh, J. A. (1986) Rev. Infect. Dis. 8: 228). The parasite's distribution is worldwide, while the preponderance of morbidity and mortality is experienced in Central and South America, Africa and India. Groups at increased risk for severe disease include the very young and old, the malnourished and pregnant women (Armon, P. J., (1978), Brit. J. Ob. Gyn. 85: 264; Walsh, J. A., (1986), Rev. Infect. Dis. 8: 228). For example in Dhaka Bangladesh invasive amebiasis is more common in children of 2–3 years of age and in adults older than 40. The overall malnutrition of the patients may have contributed to the 29% fatality rate despite hospitalization and antiamebic chemotherapy (Wanke, C. et al, (1988), Am. J. Trop. Med. Hyg. 38: 335. *E. histolytica* is also an important cause of nosocomial (hospital-acquired) infection in developing countries. *E. histolytica* was found to be the second most common cause of nosocomial diarrhea in a prospective study from the Instituto Nacional de la Nutricion in Mexico City. Mortality in patients with nosocomial diarrhea was 18%, compared to 5% in controls. The preponderance of disease in the developing world is due to fecal-oral spread of infection resulting from complex socioeconomic problems for which there are no immediate solutions. As the improvements in sanitation necessary to prevent the fecal-oral spread of enteric protozoa in the developing world are only slowly being made, control of amebiasis and other diseases is dependent upon advancements in diagnosis, treatment, and immunoprophylaxis.

The pathogenesis of amebiasis begins with cyst formation in the bowel lumen, where unicellular trophozoites undergo nuclear division to form the 4-nucleated cyst. Infection occurs when the cyst is ingested via fecally contaminated food or water. Cysts undergo further nuclear division during excystation leading to the formation of 8 trophozoites. Trophozoites multiply by binary fission. Amebic trophozoites can colonize the bowel lumen, encyst, and/or invade through the intestinal epithelium to cause colitis or liver abscess.

*Entamoeba histolytica* was named by Schaudinn in 1903 for its ability to destroy human tissues. *E. histolytica* trophozoites in vitro will kill a wide variety of tissue culture cell lines as well as human neutrophils, T lymphocytes and macrophages. Trophozoite killing of target cells is contact-dependent and extracellular. Killing of host cells by *E. histolytica* trophozoites in vitro occurs only upon direct contact, which is mediated by an amebic adhesin which recognizes N- and O-linked oligosaccharides (reviewed in McCoy et al, (August 1994) Infect. Immun. 62: in press). This adhesin is specifically inhibited by millimolar concentrations of galactose and N-acetyl-D-galactosamine-(Gal/GalNAc), and has been named the Gal/GalNAc lectin. This lectin is a heterodimer of heavy and light subunits which are encoded by multigene families designated hgl and lgl respectively.

The mechanism of contact-dependent killing by *E. histolytica* has been the subject of intensive investigation. Intracellular calcium in target cells rises approximately 20-fold within seconds of direct contact by an amebic trophozoite and is associated with membrane blebbing (Ravdin et al, (1988) Infect. Immun. 56: 1505). Cell death occurs 5–15 minutes after the lethal hit is delivered. Extracellular EDTA and treatment of the target cells with the slow sodium-calcium channel blockers verapamil and bepridil (Ravdin et al, (1982) J. Infect. Dis. 154: 27) significantly reduce amebic killing of target cells in suspension. Isolation of amebic pore-forming proteins similar in function to pore-forming proteins of the immune system has been reported by a number of laboratories. (Young et al, (1982) J. Exp. Med. 156: 1677; Lynch et al, (1982) EMBO J 7: 801; Young & Cohn, (1985) J. Cell Biol. 29: 299; Rosenberg et al, (1989) Molec. Biochem. Parasit. 33: 237; Jansson et al, (1994) Science 263: 1440). A purified 5 kDa amoebapore and a synthetic peptide based on the sequence of its third amphiphatic alpha helix have recently been shown to have cytolytic activity for nucleated cells at high concentrations (10–100 µM) (Leippe et al, (1994) Proc. Natl. Acad. Sci. U.S.A. 91: 2602). Proteolytic activities of *E. histolytica* are also believed to be involved in damage of cells and the extracellular matrix of the host. Secreted amebic cysteine proteases cause a cytopathic (as opposed to cytotoxic) effect manifest by cells being released from monolayers in vitro without cell death (Reed et al, (1989 J. Clin. Microbiol. 27: 2772; Tannich et al, (1991) J. Molec. Evol. 34: 272; McKerrow et al, (1993) Ann. Rev. Microbiol. 47: 821).

There are a number of interesting molecules implicated in pathogenesis of enteric protozoan that could be targets for vaccines or therapeutics. The development of DNA transfection methodologies promises to enable genetic validation of their importance in pathogenesis via forward and reverse genetics, enable the production of avirulent enteric protozoa (for use a live vaccines) via genetic "knock-out" of virulence factor genes, as well as set the stage for an understanding of the genetic regulation of the expression of virulence factors during infection and invasion.

To date, little is known about regions required for proper transcription and translation of enteric protozoan genes. While the function of conserved regions identified in the flanking domains of reported genes could be postulated to be involved in regulation of transcription or translation, the lack of a transfection system blocked any attempt to definitively determine the flanking sequences required for gene expression. Thus, the development of a transfection system is required before the genetic elements responsible for proper regulation, promotion, polyadenylation, and ribosomal binding of enteric protozoan genes can be determined.

The development of vaccines against enteric protozoa has been hampered by an incomplete understanding of their pathogenesis. Although several proteins have been identified which appear to be involved in colonization and virulence, in most cases their specific functions and roles in pathogenesis are poorly defined. Enteric protozoa presents a challenge to genetic analysis because there is no known sexual cycle or method to introduce foreign DNA. The ability to manipulate the parasite genome via DNA transfection would allow a more detailed analysis of the factors responsible for virulence as well as enable the production of "attenuated" or avirulent parasites for use as vaccines.

SUMMARY OF THE INVENTION

Accordingly, one object of the present invention is to provide methods for manipulating an enteric protozoan genome via DNA transfection.

A second object of the present invention is to provide transformed enteric protozoan, especially less virulent forms of such protozoan.

A third object of the present invention is to provide vaccines generated from such transformed enteric protozoan.

A fourth object of the present invention is to enable the production of foreign or altered proteins in *E. histolytica* or other enteric parasites for therapeutic uses.

A fifth object of the present invention is to provide DNA sequences which provide maximal expression of proteins in *E. histolytica*.

The present inventors have now discovered that these and other objects can be achieved by a transfection system that maximizes foreign DNA internalization and expression without destroying the fragile trophozoite. In particular, the present inventors have found that constructs containing (i) a foreign gene to be expressed (ii) flanked by at least a 5' and ideally also a 3' flanking DNA sequence(s) from a protein-encoding gene of an enteric protozoa contain the necessary elements for proper gene expression in enteric parasites.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

In the first embodiment, the present invention provides a method for transforming an enteric protozoa. The method comprises introducing an expression vector containing a construct of at least (i) a 5' and ideally also a 3' flanking DNA sequence(s) surrounding (ii) a foreign gene to be expressed in said enteric protozoa. This embodiment is based on the inventor's discovery that the flanking DNA sequence of an enteric protozoa gene which is expressed natively in an enteric protozoa can be used to confer the ability to express a gene linked thereto.

Suitable enteric parasites which can be transformed according to the present invention include any enteric protozoa such as amebae (Rhizopodea), Ciliatea such as (*Balantidium coli*) and flagellates (Mastigophora). Suitable ameba include *Entamoeba histolytica, Entamoeba dispar, Entamoeba coli, Endolimax nana, Entamoeba gingivalis, Iodamoeba bütschlii, Dientamoeba fragilis* Cyclospora species, *Cryptosporidium parvum, Isospora belli* and Microsporidic species. Of these, *Entamoeba histolytica* is preferred. Suitable flagellates include *Giardia lamblia, Chilomastix mexnili, Trichomonas tenax, Trichomonas hominis* and *Trichomonas vaginalis*.

The 5' flanking DNA sequence of hgl1, the 5' flanking DNA sequence from actin and the 5' flanking sequence of pyridine nucleotide transhydrogenase (PNK) gene are particularly preferred.

Figure 1:
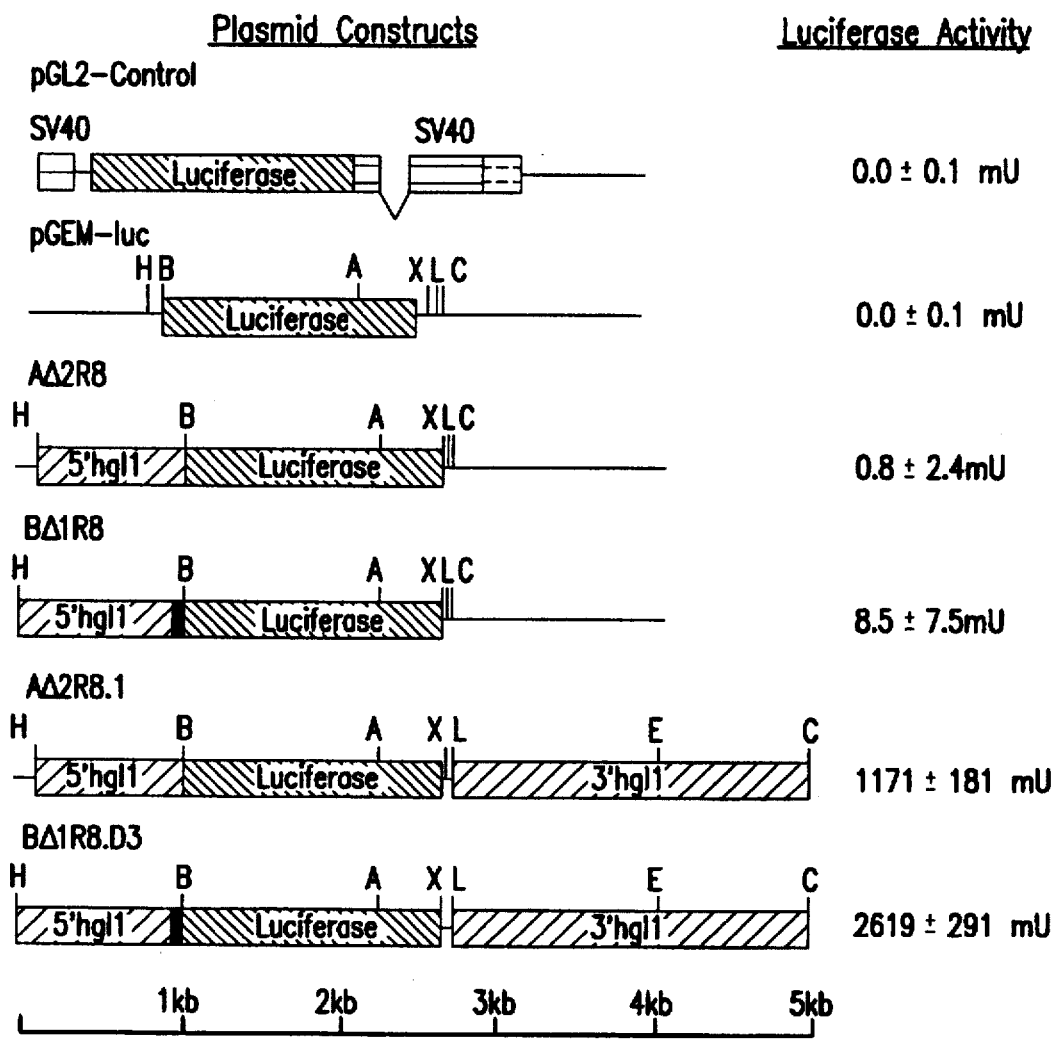
FIG. 1. Plasmid constructs used to transiently transfect *E. histolytica*. ▣, SV40 promoter; ▢, SV40 polyadenylation signal; V, intron; ▢, SV40 enhancer; ▨, luciferase coding region; ▨, 5' flanking region of hgl1; coding region of hgl1; ▨, 3' flanking region of hgl1; —, plasmid sequence; H, HindIII; B, BamHI; A, ClaI; X, XhoI; L, SalI; C, SacI; E, EcoRI.

A construct containing only the 5' flanking DNA sequence is useful for obtaining transient transfection but is suboptimal (see construct AΔ2R8 and BΔ1R8, FIG. 1).

The 3' flanking DNA sequences of the present invention contain a conserved sequence near the termination codon of the gene to be expressed. Preferably the 3' flanking DNA sequence contains at least 0.5 kb of nucleotide sequence. Suitably, the 3' flanking DNA sequences may contain one of the following sequences shown in Table 1 (SEQ ID Nos: 1–16).

TABLE 1

| 3' Flanking Sequences | |
|---|---|
| TAAgaacaaTAATTaagagaattgaataacattt | Purdy et al. (1993) Mol. Biochem. Parasitol. 62: 53–60 |
| TAActtttggAAATTaagTTATTttgttttcttt | Tannich et al. (1992) J. Mol. Evol. 34: 272–273 |
| TAActtttggAAATTaagTTATTtttgtttcatt | lg12 McCoy et al. (1993) Infect. Immun. 62: _ |
| TAAgcgtttTAATTtactttctcattt | Actin 1 Edman et al. (1987) J. Exp. Med. 172: 879 |
| TAAgtCATTTttagttt | Actin 2 Huber et al. (1987) Molec. Biochem. Parasitol. 32: _ |
| TAAgtcataagTGATTttttcattgat | Ferredoxin Huber et al. (1988) [ref.] |
| TAAacgtTAATTgaagaTATTTcatttt | Edman et al. (1990) J. Exp. Med. 172: 879–888 |
| TAAatgagtTATTTgacttt | SREHP Stanley et al. (1990) [ref.] |
| TAG . . . . aaaTAATTaataaaatTAATTatttcttcttttcc | Elongation factor De Meester (1991) [ref.] |
| TAAfTAATTTAATTatcttattattt | hg12 Tannich et al. (1991) J. Biol. Chem. 266: 4798 |
| TGAaTATTTcacagttaaatcacttctttttatg | Eh-CPp Tannich et al. (1991) J. Biol. Chem. 266: 4798 |
| TAAaacaaacaagaTAATTtaatacaaattatttt | Eh-30 Tachibana et al. (1991) [ref.] |
| TAAgtgaagtttCACTTttcccctc | Eh-FeSODp Tannich et al. (1991) J. Biol. Chem. 266: 4798 |
| TAAafTAATTgatctctttgggtg | Zinc Finger Stanley et al. (1992) [ref.] |
| TAAgttttaagctactCAATTgagtaaatttcatac | Eh-APp Leippe et al. (1992) Proc. Natl. Acad. Sci. USA 91: 2606 |
| TAA . . . . catccttttgTAATTgattttaaccttt | Ubiquitin Wostmann et al. (1992) [ref.] |

These enteric protozoa are suitably transfected with an expression vector containing a construct containing (i) at least a 5' flanking sequence operably linked to (ii) a foreign gene to be expressed. In a preferred embodiment, the construct comprises both a 5' and a 3' flanking DNA sequence operably linked to said gene.

As used herein, "expression vector" means any DNA which can be transfected and expressed into an enteric protozoa. Suitable expression vectors include a single piece of DNA in linear or circular form and may include, in addition to the construct of the present invention, selectable marker genes and/or features which assist translation such as promoters, inducible elements, etc. These additional genes/features may be heterologous or homologous to the 5' flanking DNA sequence. Reporter genes such as chloramphenicol acetyltransferase (CAT), G418 resistance gene, luciferase, β-galactosidase and the green fluorescent protein (Chalfie et al, (194) Science 263: 802) can also be included.

Figure 4:
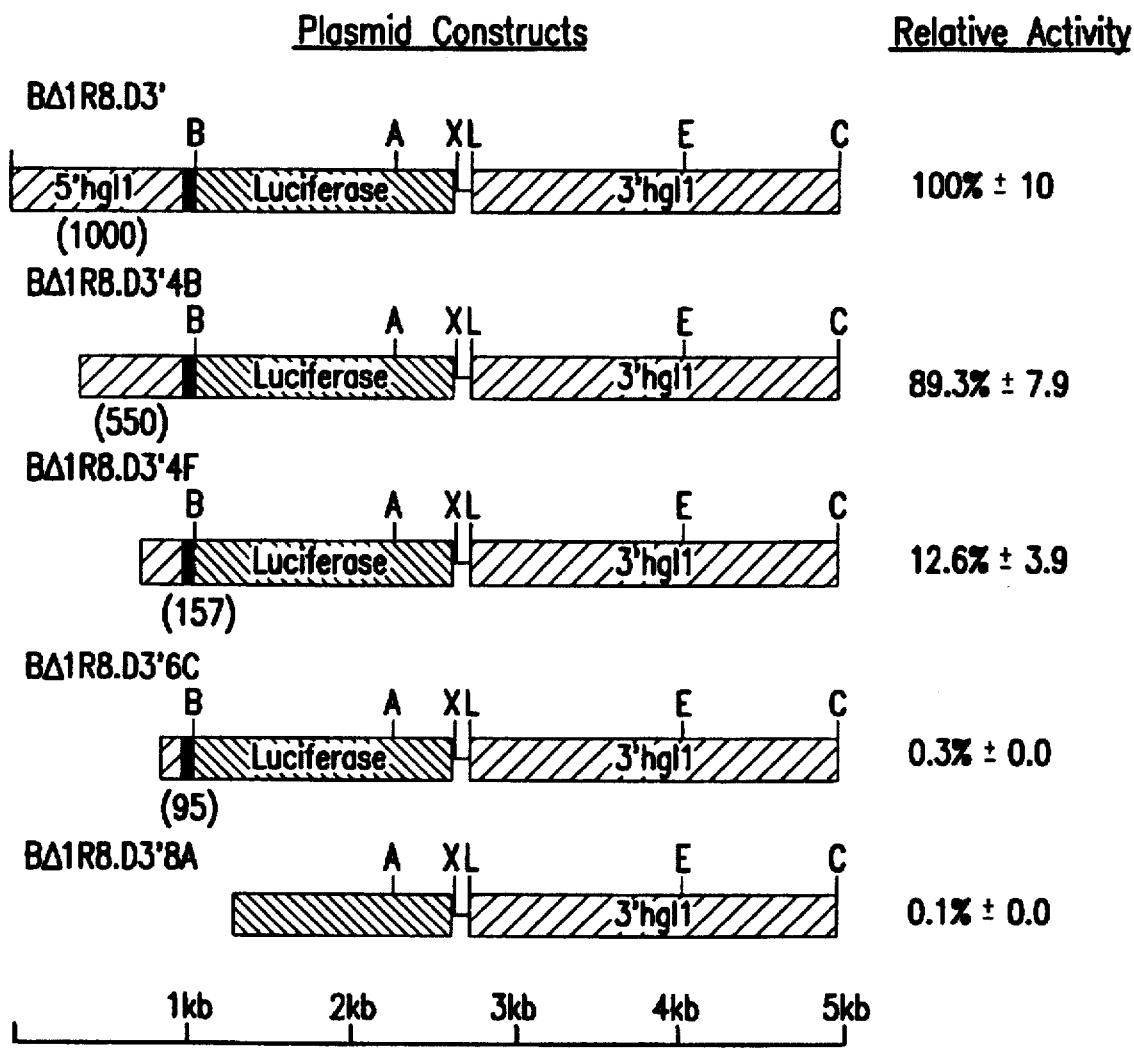
FIG. 4. 5' deletion analysis of the BΔ1R8.D3 plasmid construct. The endpoints of all deletions were confirmed by sequencing. Luciferase activity is expressed as percent of the expression (mean±S.E.; n=3) of the intact BΔ1R8.D3 plasmid measured simultaneously at 12 h after electroporation.

As used herein, "flanking DNA sequence" means a sequence of DNA which is native to an enteric protozoa and is natively found flanking a protein-encoding gene. The 5' flanking DNA sequences of the present invention contain a TATA-like sequence at approximately −30 bp from the initiation codon of the adjacent gene as well as a conserved sequence at approximately −10 bp. Suitable 5' flanking DNA sequences contain at least 0.5 kb (see construct BΔ1R8.D3'4B, FIG. 4), preferably at least 1 kb, of nucleotide sequence. Examples of 5' flanking sequences that may be used are shown in Table 1.

Suitable 5' and 3' flanking DNA sequences can be isolated by screening genomic enteric protozoa libraries with oligonucleotide probes based on their published sequences. These flanking sequences are found flanking the open reading frames of the protein encoding genes. The sequences shown above in Tables 1 and 2 are examples of such flanking sequences (the lengths of the flanking sequences shown should be understood to be partial sequences which are shorter than the recommended lengths).

A particularly preferred 5' flanking sequences is the 1 kb of 5' flanking sequence with 16 base pairs of coding sequence isolated from the hgl1 gene. A particularly preferred 3' flanking sequence is the 2.3 kb of 3' flanking sequence from hgl1.

Figure 6:
FIG. 6. 5' deletion analysis of the lectin-luciferase transfection vector. Luciferase activity resulting from the electroporation of *E. histolytica* with plasmid constructs containing a progressively shorter 5' flanking sequence was assayed for luciferase activity 10 hours after transfection. The number of bases remaining 5' of the start codon was determine by sequence analysis and is indicated in parentheses. Reported activity is expressed as a percent of the activity of BΔ1R8.D3 (mean±SE). ■, 5' flanking region of hgl1; ■, coding region of hgl1; uciferase coding region.
Figure 6:
Figure 6:
Figure 6:
Figure 6:
Figure 6:

Progressively larger deletions of the 5' flanking DNA of the hgl1 luciferase construct can be generated using restriction enzymes, for example using exonuclease III. Sequences from −287. to −201 and from −201 to −110, when absent result in greatly decreased levels of luciferase expression, while deletion from −489 to −289 increase expression 2-fold (FIG. 6). Primer extension analysis of the endogenous and transfected hgl1 mRNAs map the start of transcription to approximately −7 bases from the start of translation. Because the −489 to −287, the −287 to −201, and −201 to −110 sequences are 5' of the start of transcription, these elements contain regulatory elements for transcription.

Figure 7:
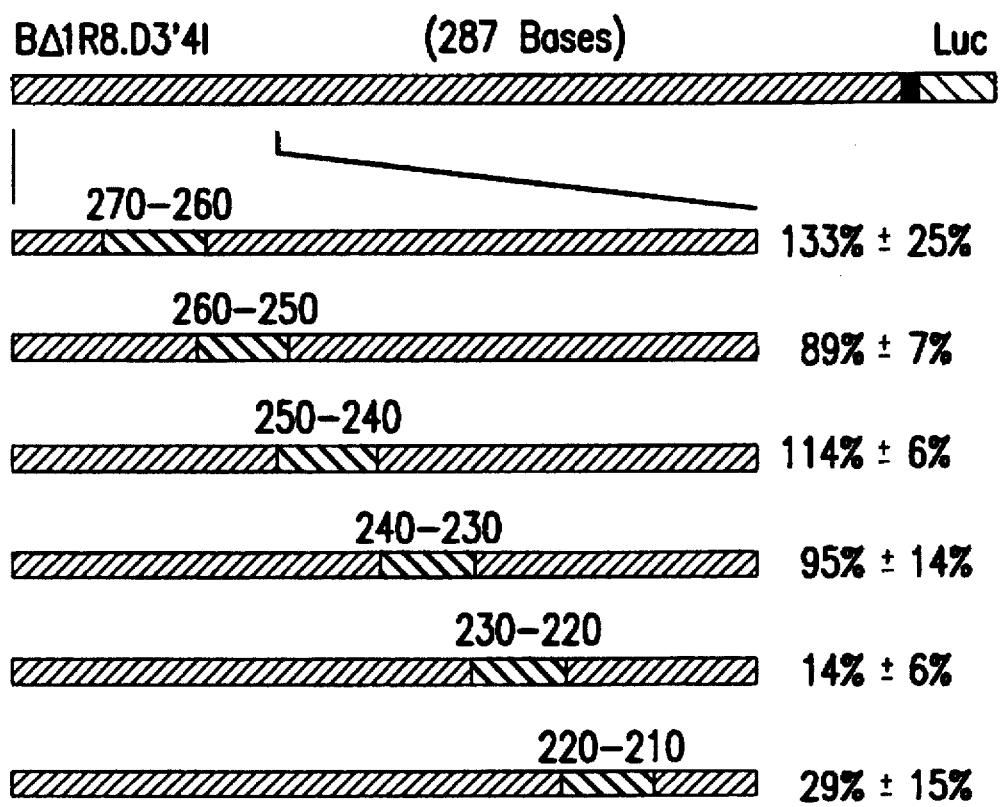
FIG. 7. Linker-scanner mutational analysis of the upstream regulatory region in between bases 201 and 287. Constructs differ from BΔ1R8.D3'41 in only a 10 base pair section (indicated in parentheses) that has been replaced with an EcoRI site. Reporter activity is expressed as a percent of the activity of BΔ1R8.D3'41 (mean±SE). Each data point represents four separate determinations. ■, 5' flanking region of hgl1; ■, area of mutation; ■, coding region of hgl1; ■, luciferase coding region.

A scanning 10 base pair substitution (containing an EcoRI site) was introduced into the 5' flanking DNA of the hgl1-luciferase construct region from bases −270 to −210 using a two step Pfu polymerase PCR amplification technique. Replacement of the sequences from −230 to −220 with the linker resulted in reduction of luciferase expression to levels seen with deletion of the entire −287 to −201 region; replacement of the −220 to −210 region resulted in partial loss of luciferase expression (FIG. 7) demonstrating that the region from −230 to −210 contains a positive regulatory element for transcription.

Thus, preferably base pairs −287 to −0 of the 5' flanking sequence isolated from a protein-encoding gene of enteric protozoa are used as 5' flanking sequence.

In accordance with the invention, the 5' and 3' flanking DNA sequences are used in conjunction with a gene of natural or synthetic origin, or a combination of the two. Suitable genes to be expressed include luciferase, hygromycin, methotrexate and neomycin resistance genes. The drug resistance genes function as selectable markers, as enteric protozoa are sensitive to these antibiotics; for example, *E. histolytica* is sensitive to neomycin, with 100% kill at concentrations ≧3 µg/mn. These genes can be obtained from Promega Inc. The use of selectable marker genes will enable stable transformation of enteric protozoa.

Figure 5:
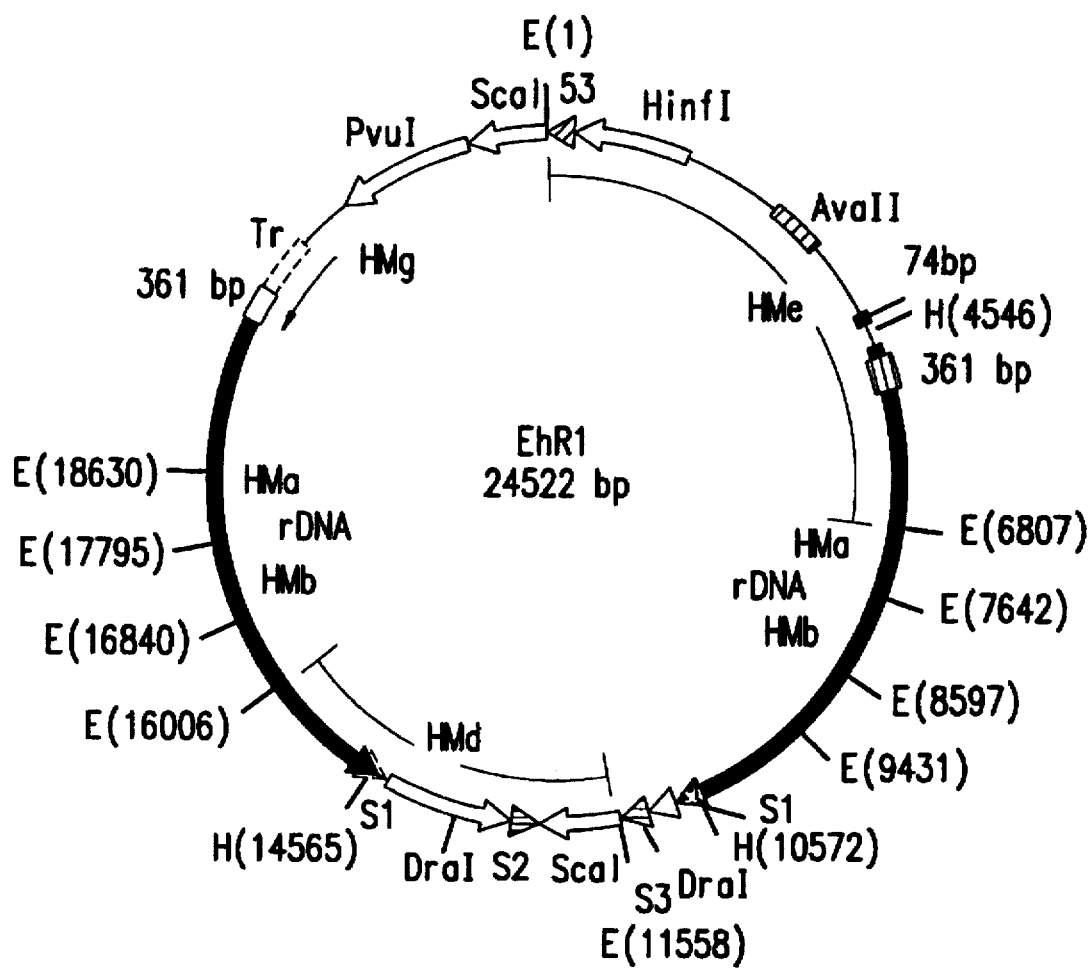
FIG. 5. Restriction map of the rDNA episome of *E. histolytica*. The locations of the EcoRI fragments that exhibit ARS activity in yeast (HMe and HMd) are shown inside the circle. E (EcoRI), H (HindIII).

A fragment of, or the intact enteric protozoan ribosomal DNA (rDNA) episome, will be ligated to the expression vector and transfected into the parasite. For example, the ribosomal RNA gene of *E. histolytica* is located in a circular extrachromosomal 24.5 kB molecule present in approximately 200 copies/trophozoite (Bhattcharya et al, (1989) J. Protozool. 36: 455; Huber et al, (1989) Molec. Biochem. Parasitol. 32: 285). Each episome contains two copies of the ribosomal genes and repetitive elements which occur in spacer regions, have tandem repeats, are variable between strains. Replicative intermediates of the rDNA episome have been detected in the 6.8 kB EcoRI fragment (HMe) of the ribosomal DNA episome by its anomalous migration on two dimensional agarose gel electrophoresis, suggesting that this fragment is near the origin of replication. The 4.4 kB EcoRI fragment (pHMd) of the rDNA contains a stretch of tandem DraI repeats which are downstream of the rRNA transcription units and which also have sequence similarities to yeast and Paramecium ARS, and which also have been shown to function as an ARS in the yeast *S. cerevisiae*. The restriction map of the rDNA episome of *E. histolytica* is shown in FIG. 5. Fragments of the intact rDNA episome, preferably HMd and/or HMe, can be included in the expression vector. The advantage of using rDNA episome sequences in the expression vector is that these sequences will allow multi-copy stable episomal expression of the expression vector.

The flanking sequences of the present invention can be linked to the genes to be expressed using conventional recombinant DNA techniques. Suitable techniques are described in Sambrook, J. et al., (1989) "Molecular Cloning. A Laboratory Manual", second edition, Cold Spring Harbor Laboratory Press: Cold Spring Harbor, N.Y. The gene to be expressed can be linked directly to the flanking sequence(s) or can be linked via intervening nucleotides. Preferably, the gene to be expressed is linked in an uninterrupted manner to the 5' flanking DNA sequence by approximately 16 bases of any Entamoeba protein encoding region (open reading frame starting at the AUG start codon) fused in frame to the open reading frame of the foreign gene to be expressed. The open reading frame of the foreign gene to be expressed should be followed 14 bases downstream of the foreign gene stop codon by the 3' flanking region of the Entamoeba protein encoding gene. "Operably linked" as used herein, means that the flanking sequence(s) and gene are linked in such a manner that the construct can be stably maintained in the host enteric protozoa and the gene is expressed.

The construct of the present invention can be inserted into plasmids. These constructs can be inserted into plasmids using conventional recombinant DNA techniques. Suitable techniques are described in detail in Sambrook, J. et al. (1989), "Molecular Cloning. A Laboratory Manual", Second Edition, Cold Spring Harbor Laboratory Press: Cold Spring Harbor, N.Y.

The plasmids of the present invention comprise a 5' flanking DNA sequence (containing upstream regulatory regions, the promoter and the ribosome binding sequence) fused to the beginning of the open reading frame of an Entamoeba gene (allowing protein translation to begin with amebic codons which are very A-T rich) followed by the foreign gene's open reading frame. Preferably the plasmid contains 3' flanking DNA sequence at the 3' end of the construct ligated very close (within 14 bases) of the stop codon of the foreign gene, since this 3' flanking DNA contains the Entamoeba transcription termination and mRNA polyadenylation sequences required for the production of stable amebic mRNA.

The plasmids of the present invention can further comprise a selection marker to determine if stable transfection has occurred. Preferred selection markers include the neomycin resistance gene or the hygromycin resistance gene.

The plasmids of the present invention may contain other features as the plasmid backbone is relatively unimportant for expression of the gene. Any conventional plasmid is suitable. For example, suitable plasmids can be purchased from Promega Corporation Madison, Wis.).

Plasmid BAIR8.D3 containing a construct in accordance with the present invention was deposited as *E. coli* strain MC 1061 under the provisions of the Budapest Treaty on Jul. 6, 1994 at the American Type Culture Collection, 12301 Parklawn Drive, Rockville, Md. 20852 under accession number 69653. Plasmids pTCV1 and pTCV2 according to the present invention were likewise deposited with the ATCC on Feb. 10, 1995 under accession numbers 97050 and 97051, respectively.

The plasmids of the present invention can be introduced into the enteric protozoa by any standard technique used to introduce foreign DNA into cells including electroporation, lipofection (Felgner et al, (1987) Proc. Natl. Acad. Sci. U.S.A. 84:7413), DEAE dextran (Sambrook et al, (1989) "Molecular Cloning: A Laboratory Manual", 2 ed., Cold Spring Harbor Laboratory Press, New York) etc. Preferably electroporation is used.

Electroporation is suitably conducted in accordance with the procedures of Van den Hoff et al (Nucleic Acid Res. (1992) 20: 2902). To obtain optimal insertion of the plasmid into the enteric parasites, the Van den Hoff et al procedure is modified such that incomplete cytomix can be made with the following formula: 120 mM KCl, 0.15 mM $CaCl_2$, 10 mM $K_2HPO_4/KH_2PO_4$, pH 7.5; 25 mM HEPES, 2 mM EGTA, 5 mM $MgCl_2$, total pH 7.8–7.9. Incomplete cytomix is preferred because it appears to be more effective than complete cytomix due to the unique biochemistry of the enteric parasites which appear to lack glutathione and utilize pyrophosphate and several steps of glycolysis (Petri and Ravdin, (1987) Eur. J. Epidemiol. 3: 123). Incomplete cytomix containing DEAE-dextran, preferably 3.1 µg/ml DEAE-dextran, provide the best system for electroporation. Plasmid concentrations of 10–80 µg/cuvette are particularly preferred for obtaining insertion of the plasmid to the host cell. Transfection is achievable using a capacitance of 250 µF–960 µF, preferably 500 µF, and a voltage of 250–1000 v/cm, preferably 500 v/cm resulting in a time constant of 5-15 msec, preferably about 10 msec. For best results the electroporation is repeated once.

Transfection of an enteric protozoa with a plasmid containing the construct of the present invention allows identification of amebic genes that may be therapeutic targets or useful in vaccines by "gene knockouts" and/or genetic complementation of avirulent or mutant ameba. Gene knockouts are accomplished by homologous recombination between the parasite chromosome and an expression vector which contains the 5' and 3' flanking DNA from a virulence factor-encoding gene surrounding a selectable marker. It also allows the production of avirulent ameba for vaccine use by knockouts of virulence genes. Targets for such knockouts include, but are not limited to, the genes encoding amebic adhesion, amebic pore-forming proteins, and amebic proteases.

The DNA constructs of the present invention, once introduced into the host cell, can exist either as chromosomal DNA or as episomal DNA. Use of rDNA episome sequences in the expression vector will enable episomal maintenance and expression. Expression vectors, such as the aforementioned plasmids, containing rDNA can be used to shuttle DNA between various hosts. For example, a plasmid in accordance with the present invention which contains a foreign gene to be expressed from *E. histolytica* can be transfected into *E. coli*, mutagenized using known techniques, reisolated and subsequently transfected into *E. histolytica*.

Host cells which are transfected with the construct of the present invention can be screened using conventional techniques. For example, when the gene to be expressed is a gene which confers resistance to a particular antibiotic, screening can be accomplished by gradually or immediately increasing the concentration of that particular antibiotic.

Confirmation that gene knockout or gene complementation has occurred can be obtained by Southern blots of restriction enzyme-digested DNA from the transformed parasite (see Sambrook et al, (1989) "Molecular Cloning: A Laboratory Manual", 2 ed., Cold Spring Harbor Laboratory Press, New York ).

In a second embodiment, the present invention provides transformed enteric protozoa. These enteric protozoa can be less virulent than wild-type enteric protozoa.

In a third embodiment of the present invention, the transformed enteric protozoa can be used to generate vaccines against enteric protozoa-mediated diseases. Since the transformed enteric protozoa are less virulent, these transformed microorganisms can be used as "modified" forms. Conventional techniques can be used to generate live vaccines using the modified forms of the enteric protozoa. Alternatively, the transformed enteric protozoa can be destroyed and used to formulate killed vaccines using conventional techniques. In yet another embodiment, polypeptides or fragments thereof from the transformed enteric proeozoa can be isolated and formulated into synthetic vaccines using conventional techniques. Conventional techniques for preparing vaccines can be used such as those described in *New Generation Vaccines*, Woodrow and Levine, Eds., Marcel Dekker, Inc.: New York, 1990.

In a fourth embodiment, the transformed enteric protozoa of the present invention can also be used to provide systems for the expression of altered or foreign genes in *E. histolytica* and other enteric parasites. These expressed products could be used therapeutically.

Having generally described this invention, a further understanding can be obtained by reference to certain specific examples which are provided herein for purposes of illustration only and are not intended to be limiting unless otherwise specified.

EXAMPLES

Example 1

Expression of firefly luciferase in *E. histolytica*

Cell Culture Conditions. *E. histolytica* strain HM-1:IMSS trophozoites were grown in TYI-S-33 medium containing penicillin (100 U/ml) and streptomycin sulfate (100 µg/ml) in 75 cm$^2$ flasks at 37° C. (Diamond, L. S. et al. (1978) Trans. R. Soc. Trop. Med. Hyg. 72: 431). Amebae in log phase growth were used for transfection experiments after they had grown to 5.3–6.6×10$^4$ trophozoites/ml.

Plasmid Construction. Plasmid pGEM-luc, which contains the luciferase gene, and plasmid pGL2-Control, which contains the luciferase gene flanked by an SV40 promoter, polyadenylation signal, and enhancer, are commercially available (Promega Corp. Madison, Wis.). To make plasmid ΔR8 (all constructs are illustrated in FIG. 1), the 3' portion of the luciferase gene from pGEM-luc was amplified by polymerase chain reaction (PCR) using the primers 94 and 95 (all nucleotides used for plasmid construction are described in Table 2) which added a synthetic XhoI site in the amplified product two bases 3' of the stop codon of luciferase (SEQ ID Nos: 17–23).

TABLE 2

Oligonucleotide primers used in the construction of plasmids shown in FIG. 1

| Name | Sequence | Description |
|---|---|---|
| 94 | TGGCCCCCGCTGAATTG | Nucleotides 393 to 409 of luciferase coding region of pGEM-luc |
| 95 | gcgcgcctcgagTTTTACAATTTGGACTT | Nucleotides 116 to 100 of luciferase coding region of pGEM-luc, XhoI site, reverse primer |
| 96 | gcgcgcaagcttTTTGATAAGTCATGAGT | Approximately −1000 bases 5' of hgl1 start codon, HindIII site |
| 98 | gcgcgcggatccCTTTCTAGTTCATTGTC | Nucleotides −9 to −25 relative the start codon of hgl1, BamHI site, reverse primer |
| 99 | gcgcgcgagctcACGATGTAACTCAATAA | Approximately 2300 bases 3' of the hyl1 stop codon, SacI site, reverse primer |

TABLE 2-continued

Oligonucleotide primers used in the construction of plasmids shown in FIG. 1

| Name | Sequence | Description |
|---|---|---|
| 118 | gcgcgcggatccATAATAATAATTTCATAT | Nucleotides +16 to −2 relative to the start codon of hgl1, BamHI site, reverse primer |
| 131 | gcgcgcgtcgacGAACAATAATTAAGAGAATT | Nucleotides 1 to 18 3' of the hgl1 stop codon, SalI site |

All nucleotides are in 5' to 3' orientation. Primers which are reverse anti-sense to the coding strand are referred to as ' reverse primers.' Lower case letters indicate nonhomologous sequences with restriction sites underlined and listed under description.

The amplified product and pGEM-luc were digested with ClaI and XhoI and ligated together with T4 DNA ligase (Gibco-BRL). By effectively deleting 53 bases between the stop codon of the luciferase gene and the XhoI site in the multicloning site of pGEM-luc, 3' amebic sequences could be ligated in close proximity to the 3' terminus of the reporter gene. A short 3' untranslated region in amebic mRNA is typical and may prove critical to message stability. To make the AΔ2R8 construct, approximately 1 kb of the 5' flanking region of hgl1 was PCR amplified from a genomic clone containing the 5' coding region and flanking region of hgl1 (Purdy, J. E. et al. (1993) Mol. Biochem. Parasitol. 62: 53), using the primers 96 and 98. The amplified product and ΔR8 were digested with BamHI and HindIII and subsequently ligated producing plasmid AΔ2R8. This placed the 5' non-coding region of hgl1 5' of the reporter gene at the expense of replacing bases −1 through −8 of the hgl1 gene with the restriction site BamHI. Plasmid BΔ1R8 was constructed by PCR amplification of approximately 1 kb of the 5' flanking region of hgl1 as well as the first 16 bases of the hgl1 coding region using the primers 96 and 118. This product and ΔR8 were digested with HindIII and BamHI and ligated. This construct contained in order 5' to 3': an unaltered 5' non-coding region of hgl1, the first 5 codons of hgl1, 3 in frame codons created by the ligation of the synthetic BamHI restriction site to hgl1 and luciferase DNA, and the in frame methionine codon of luciferase. Not only is the 5' flanking region unaltered in this construct, but a hgl1/luciferase fusion protein should result allowing the amebic ribosome to initiate using the amebic codon bias before beginning translation of the foreign protein. To construct BΔ1R8.D3, the 3' flanking region of hgl1 was PCR amplified from a genomic clone containing the 3' coding and flanking region of hgl1 (Purdy, J. E. et al. (1993) Mol. Biochem. Parasitol. 62: 53) using the primers 131 and 99. The product and BΔ1R8 were digested with SalI and SacI and ligated together. This placed the 3' non-coding region of hgl1 14 bases 3' of the reporter gene. Plasmid AΔ2R8.1 was constructed by restriction digestion of BΔ1R8.D3 and AΔ2R8 with SalI and SacI. The 2.3 kb insert (3' flanking region of hgl1) from BΔ1R8.D3 and the AΔ2R8 plasmid were purified on an agarose gel and ligated together.

The structures of all constructs were confirmed by restriction digestion and all points of ligation were confirmed by DNA sequence analysis. Plasmids used for electroporation were isolated via alkaline lysis followed by purification on an anion exchange column (either Maxi tip-500 or Mega tip 2500) according to the manufacturers instructions (Qiagen, Chatsworth, Calif.). All preparations were assayed for purity and plasmid concentration by spectrophotometer. No luciferase activity was detectable in the purified plasmid preparations prior to transfection.

Electropotation. Log phase trophozoites were incubated on ice for 15 minutes in TYI-S-33 medium, centrifuged at 200×g for 5 minutes, and washed one time in incomplete cytomix [120 mM KCl; 0.15 mM $CaCl_2$; 10 mM $K_2HPO_4KH_2PO_4$, pH 7.5; 25 mM. Hepes; 2 mM EGTA; 5 mM $MgCl_2$; total pH 7.8–7.9]. Complete cytomix, containing 2 mMATP and 5 mM glutathione (van den Hoff, et al. (1992) Nucleic Acids. Res. 20: 2902) was used for comparison. Trophozoites were resuspended in incomplete cytomix at a concentration of 2.6–2.8 $10^6$/ml and 0.8 ml was placed into 0.4 cm electroporation cuvettes (Bio-Rad, Melville, N.Y.) on ice. 40 µg of plasmid or distilled water and 2.5 µl of 1 mg/ml DEAE-dextran (Gauss, G. H. et al. (1992) Nucleic Acids Res. 20: 6739) were added and the media mixed immediately prior to electroporation. Standard electroporation conditions were 500 µF and 500 V/cm with a Gene Pulser augmented with a capacitance extender (Bio-Rad), resulting in a time constant of 9.7–10.6 msec. Cuvettes were placed back on ice for 15 minutes after which the electroporated trophozoites were added to 11 ml of TYI-S-33 medium containing penicillin, streptomycin sulfate, and 8 µM (2S, 3S)-trans-epoxysuccinyl-L-leucylamido-3-methyl-butane (E-64c, Sigma, St. Louis, Mo.) in capped glass tubes. 100–150 µl of pre-electroporated cytomix and post-electroporated trophozoites were spread on a Luria broth (LB) bacterial plate and aliquots of cytomix were added to LB-broth and TYI-S-33 media to confirm the lack of bacterial contamination.

For control experiments, 18–36 units of RNase (Boehringer Mannheim Biochemica, Indianapolis, Ind.) were added prior to electroporation, cycloheximide (Sigma) was added (100 µg/ml) to culture media (Soldati, D. et al. (1993) Science 260: 349), amebae were treated the same without electroporation, or cytomix was electroporated alone. In each case, cefotaxime (Claforan, Hoeschst-Roussel Pharmaceuticals, Somerville, N.J.) was added (100 µg/ml) to culture media.

Luciferase Assay. Transfected trophozoites in TYI-S-33 medium were centrifuged at 200×g for 5 minutes and washed one time in PBS, pH 7.5. The trophozoite pellet was resuspended in an equal amount of 1×lysis buffer [25 mM Tris-phosphate, pH 7.8; 2 mM 1,4-dithiothreitol (DTT); 2 mM 1,2-diaminocyclohexane-N,N,N',N'-tetraacetic acid; 10% glycerol, 1% Triton X-100] containing 75 µM trans-epoxysuccinyl-L-leucylamido-(4-guanidino)butane (E-64, Sigma) and 0.75 µg/ml leupeptin (Sigma). Samples were immediately frozen at −20° C. for a minimum of one hour, thawed on ice for 10 minutes, centrifuged briefly to pellet debris, and returned on ice for an additional 10 minutes. After warming to room temperature for 10 minutes, 20 µl of the amebic lysate was assayed in 100 µl of luciferase assay reagent [20 mM Tricin, 1.07 mM $(MgCO_3)_4Mg(OH)_2 \cdot 5H_2O$, 2.67 mM $MgSO_4$, 0.1 mM EDTA, 33.3 mM DTT, 270 µM coenzyme A, 470 µM luciferin, 530 µM ATP, final pH 7.8] (Promega) using a Turner Luminometer Model TD-20e (Promega). Background luminescence on the luminometer was calibrated to zero immediately prior to all assays with *E. histolytica* electroporated without plasmid. The luciferase activity was calculated from a standard curve obtained before each experiment using the same substrate and exogenous firefly luciferase (ca. $1\times10^7$ luciferase light units/mg luciferase, Boehringer Mannheim Biochemica). To assay for luciferase secretion, growth media was assayed for luciferase activity with negative results.

Figure 2:
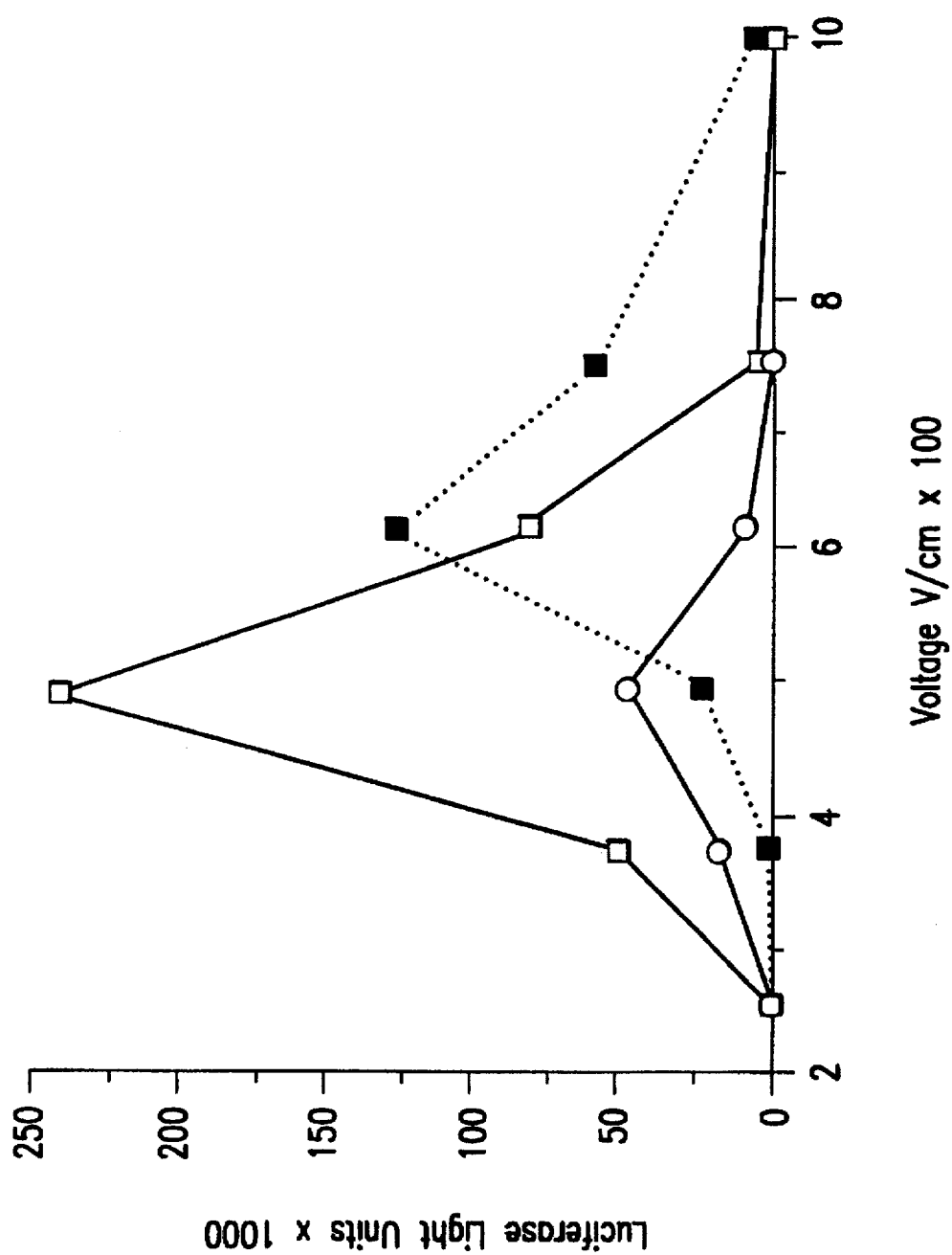
FIG. 2. Optimal voltage and capacitance for electroporation. Amoebae in log growth phase were electroporated at various combinations of voltage and capacitance in the presence of 40 μg of BΔ1R8.D3. They were harvested after 6 hours and assayed for luciferase activity. Results are expressed as luciferase light units/2.1–2.3×10⁶ amebae transfected. Each determination is representative of between three to five similarly performed experiments. ○, 960 μF; □, 500 μF; ■, 250 μF.

Optimal Electrical Conditions of Electropotation. Amebic trophozoites harvested from log-phase growth cultures were electroporated with the BΔ1R8.D3 plasmid (40 µg/2.1–2.3× $10^6$ trophozoites) under a wide variety of electrical settings to determine the conditions yielding maximal luciferase expression. The optimal voltage and capacitance were determined to be 500 µF and 500 V/cm (200 V/0.4 cm cuvette) (See FIG. 2). At these conditions, the average time constant (related to capacitance and resistance) was 10.0 msec with the trophozoite rate of survival based upon visual inspection 25–35%. Electroporation with 125 µF, 25 µF, and 3 µF capacitances resulted in suboptimal levels of luciferase activity at all voltages assayed.

Optimal Electropotation Buffer. The amebae were resuspended in incomplete cytomix for all electroporation experiments reported. Electroporation using complete cytomix (van den Hoff, M. et al. (1992) Nucleic Acids Res. 20: 2902) resulted in luciferase activity 10–15% of that seen when incomplete cytomix was used (data not shown). DEAE-dextran, which is thought to increase the local concentration of DNA at the cell surface (Gauss, G. H. et al. (1992) Nucleic Acids Res. 20: 6739), was added to each cuvette prior to electroporation (3.1 µg/ml) as it resulted in luciferase activity 58% greater than the activity observed when no DEAE-dextran was present. Final DEAE-dextran concentrations of 10 µg/ml and 5 µg/ml decreased luciferase activity by 96% and 5% respectively from the activity observed when no DEAE-dextran was present. Luciferase activity increased linearly with plasmid concentrations of 10 µg/cuvette to 60–80 µg/cuvette using the described conditions.

Figure 3:
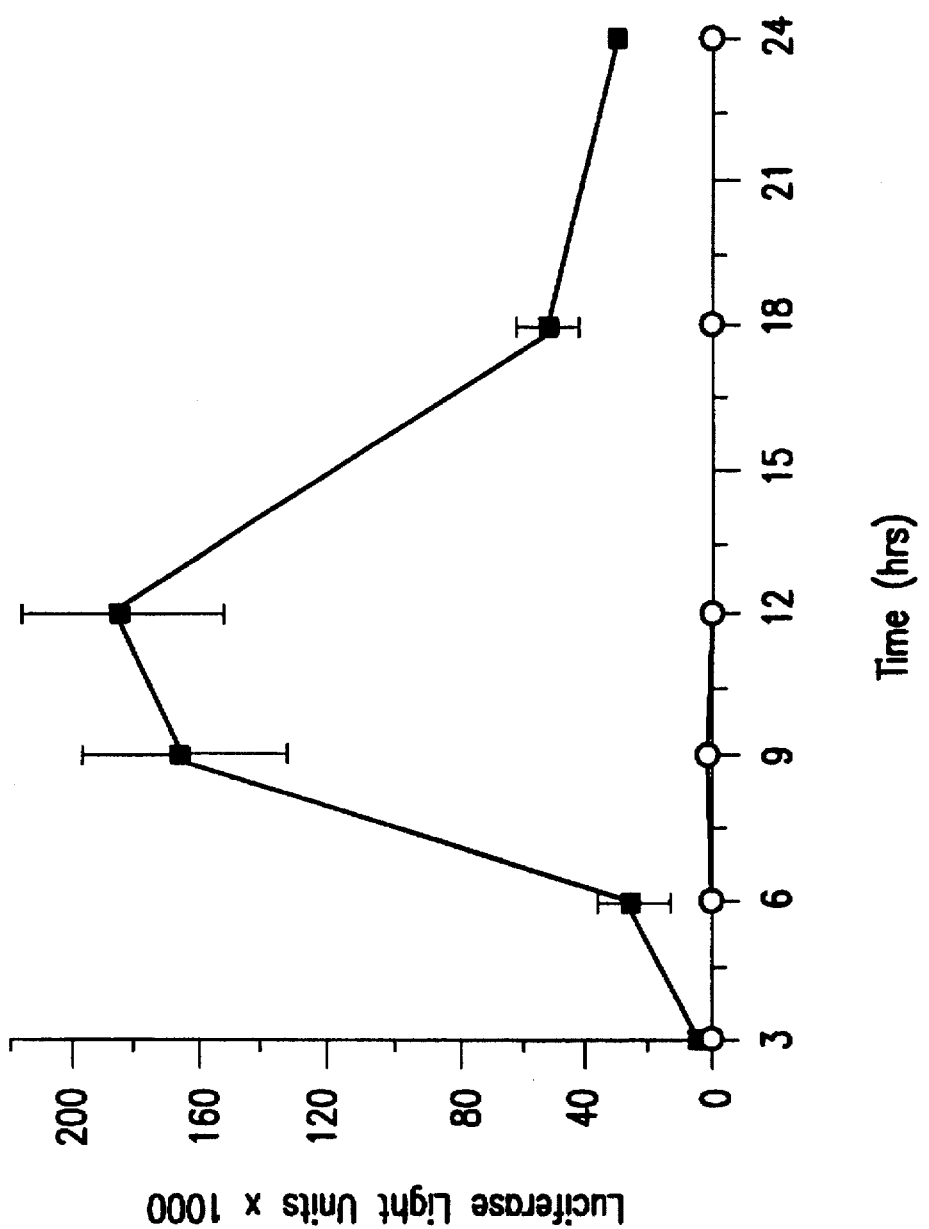
FIG. 3. Time course of luciferase expression post-electroporation. Amebae in log growth phase were electroporated at 500 μF and 500 V/cm with 40 μg of BΔ1R8.D3 or pGEM-luc, then harvested at various time points and assayed for luciferase activity. Results are expressed as luciferase light units/2.1–2.3×10⁶ amebae transfected. Each point represents three assays. ■, BΔ1R8.D3; ○, pGEM-luc.

Time Course of Luciferase Expression. Amebae were electroporated at the optimal electrical and buffer conditions and the luciferase activity assayed at different time points. The pGEM-luc plasmid which lacked amebic sequences resulted in background levels of luciferase activity at each assay (see FIG. 3). Luciferase activity after electroporation with the BΔ1R8.D3 construct was not detectable prior to 3 hours, peaked at 9 to 12 hours post-electroporation with luciferase activity 200 to 5000-fold greater than that seen with the pGEM-luc plasmid, and decreased to 20-fold over background by 24 hours.

Protease Inhibitors. *E. histolytica* produces significant amounts of cysteine proteases (Keene, W. E. et al (1986) J. Exp. Med. 163: 536). The addition of up to 40 µg of exogenous luciferase to amebic lysate resulted in only background levels of activity due to rapid digestion of luciferase (data not shown). Protease inhibitors were tested to determine the concentration that would maximally inhibit amebic proteases while minimally inhibiting luciferase. This was accomplished by resuspending trophozoites in lysis buffer, adding protease inhibitors alone, in combination, and at different concentrations, adding exogenous luciferase, and assaying for activity. Of the protease inhibitors assayed [phenylmethylsulfonyl fluoride, ethylenediaminetetraacetic acid, p-hydroxymercuribenzoic acid, ethylene glycol-bis(β-aminoethyl ether)N,N,N'N'-tetraacetic acid, trypsin inhibitor, p-chloromercuriphenyl-sulfonic acid, N-ethylmaleimide, E-64, 4-(2-aminoethyl)benzenesulfonyl fluoride, and leupeptin], it was found that concentrations of 37.5 µM of E-64 and 0.375 µg/ml of leupeptin were optimal, retaining approximately 50% of the exogenous luciferase activity.

As these protease inhibitors were not present prior to lysis, it was reasonable to assume that luciferase degradation was also occurring in the trophozoites prior to this step. Thus E-64c, an inhibitor similar to E-64 but able to cross cellular membranes, was added to the TYI-S-33 medium in which the amoebae were placed immediately after electroporation. Concentrations of E-64c between 1.4 µM and 10.6 µM increased luciferase activity after electroporation, with the optimal concentration of 8 µM increasing luciferase activity by 550%.

Control Transfections. The addition of the broad-spectrum antibiotic cefotaxime (100 µg/ml) to amebic culture media after transfection of BΔ1R8.D3 resulted in no decrease in luciferase activity, suggesting that electroporation of contaminating bacteria was not an explanation for observed luciferase activity. Additionally, bacteria were not detected when the electroporation buffer was spread on rich bacterial plates or inoculated into rich bacterial media. The addition of RNase (18–36 units/cuvette) prior to transfection of amoebae with BΔ1R8.D3 did not decrease luciferase activity indicating this activity was not due to contamination of plasmid DNA by *E. col*-produced luciferase mRNA transcripts. In fact, the addition of RNase increased luciferase activity from 86.3 mU±12.3 (x±S.E., n=3) to 79.6 mU±152.5 due to glycerol in the RNase stock which increased amebic survival. When glycerol alone was added to amoebae prior to electroporation, luciferase activity increased by a similar amount. The addition of cycloheximide (100 µg/ml) after transfection of B×1R8.D3 resulted in luciferase activity of 0.0 mU±0.2 indicating that luciferase is dependent upon eukaryotic protein synthesis machinery. Unelectroporated amoebae or cytomix electroporated without amoebae resulted in only background levels of activity (1.6 mU±0.1 and 0.6 mU±0.3 respectively) indicating that bacterial contamination of buffers or contamination of plasmid or amoebae with luciferase protein was unlikely.

Dependence on Amebic Flanking Sequences for nuciferase Expression. To determine which regions of hgl1 were required for expression of the luciferase gene, 2.1–2.3× $10^6$ amoebae/cuvette were electroporated with 40 µg of each plasmid construct at the optimal electropotation conditions and harvested after 9 hours. The resultant luciferase activity is shown in Table 3.

TABLE 3

Expression of transfected plasmid constructs.

| Plasmid | mU/transfection | S.E. | n |
|---|---|---|---|
| pGL2-Control | 0.0 | 0.1 | 3 |
| pGEM-luc | 0.0 | 0.1 | 3 |
| AΔ2R8 | 0.8 | 2.4 | 3 |
| BΔ1R8 | 8.5 | 7.5 | 3 |
| AΔ2R8.1 | 1171.3 | 180.9 | 6 |
| BΔ1R8.D3 | 2619.4 | 291.0 | 6 |

Amoebae were electroporated in cytomix containing 0.375% glycerol and assayed for luciferase activity. Activity is expressed as luciferase light units/2.1–2.3×$10^6$ amoebae transfected. S.E., standard error; n, number of determinations.

The pGL2-control construct which contains an SV40 promoter, enhancer, and polyadenylation signal is readily expressed in most eukaryotic systems. However, this construct resulted in no detectable luciferase activity in *E. histolytica*. The construct that lacked any promoter or polyadenylation sequences, pGEM-luc, also resulted in background levels of luciferase activity. The addition of the 5' flanking region of hgl1 to the pGEM-luc construct (AΔ2R8), resulted in luciferase activity slightly over background (see Table II). As this construct required the replacement of hgl1 bases −1 through −8 with a restriction site, which destroyed part of a conserved region (Edman, U. et al (199) J. Exp. Med. 172: 879), plasmid BΔ1R8 was constructed that contained all of the 5' flanking region of hgl1 present in AΔ2R8, the conserved sequence which had been altered in AΔ2R8, and 16 based of hgl1 coding region 5' of the start codon of luciferase. This effectively moved the restriction site out of the 5' flanking region of hgl1 and placed it 5 amino acids into an hgl1/luc fusion protein. Transfection with BΔ1R8 resulted in an average luciferase activity 10-fold greater than that observed for AΔ2R8 (see Table II).

In an attempt to further increase luciferase expression, 2.3 kb of the 3' flanking region of hgl1 was ligated 3' of the stop codon of luciferase in the construct AΔ2R8, creating construct AΔ2R8.1. When this construct was electroporated into amoebae, luciferase activity increased to 1171.3 mU/reaction or more than 2000-fold greater than background levels of luminescence. A similar finding was observed when the same 2.3 kb of hgl1 3' flanking sequence was ligated 3' of the luciferase stop codon in construct BΔ1R8 creating construct BΔ1R8.D3. Luciferase activity resulting from transfection of amoebae with BΔ1R8.D3 was over 300-fold greater than that observed from BΔ1R8 plasmid in amoebae.

Example 2

Production of a stable transfection system using a selectable marker (G418)

The antibiotic G418 can be used as a selectable marker for *E. histolytica*

To determine if the G418 resistance gene (neo) could be used as a selectable marker for stable transfection, G418 (0–50 μg/ml) was added in serial dilutions to a cloned HMI:IMSS *E. histolytica* strain grown in TYI-S33 medium. After 72 h of growth at 37° C., G418≧3 μg/ml killed 100% of the trophozoites. This demonstrates that *E. histolytica* is quite sensitive to G418, and neo is a suitable selectable marker for stable transfection.

Figure 8:
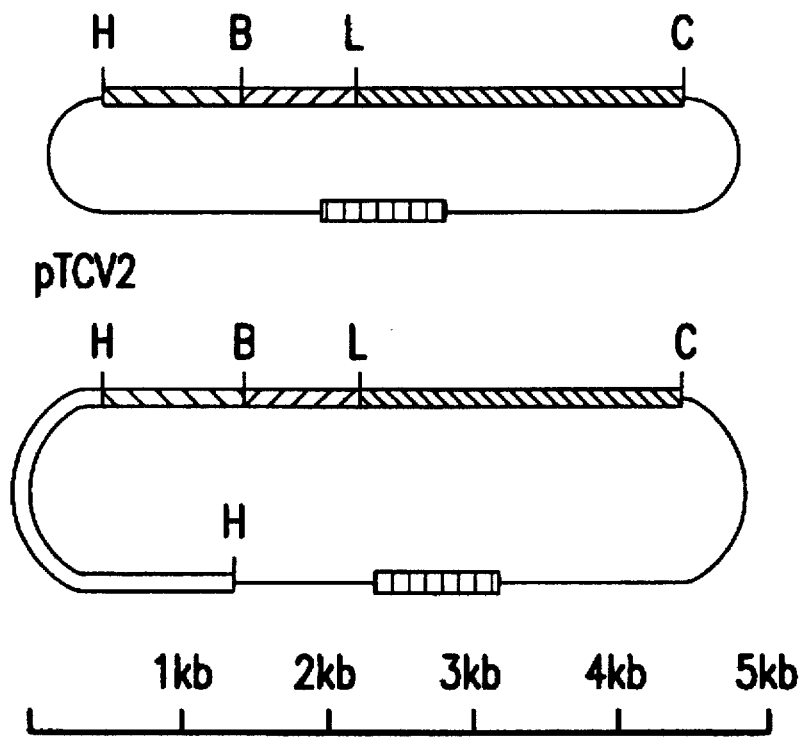
FIG. 8. Plasmid constructs used for stable transfection of *E. histolytica*. □, putative ARS-containing HMd fragment of rDNA episome; ▨, 5' flanking region of hgl1; ■, neo gene; ■, 3' flanking region of hgl1; ▨, β-lactamase gene. H, HindIII; B, BamHI; L, SalI; C, SacI.

Stable transfection of *E. histolytica* has been achieved using hgl1 neo constructs:

Ligation of neo in frame, and in place of the luciferase coding region in construct AΔ1R8.D3, resulting in the stable transfection vector pTCV1 (FIG. 8). A second construct with the HMd fragment of the rDNA episome (containing a putative origin of replication and repetitive DraI repeats to target integration into the rDNA episome) was also produced (pTCV2, FIGS. 5 & 8). The correct ligations were confirmed by sequencing over the sites of ligation. These two plasmid constructs express neo under the control of amebic cis-acting sequences, and when electroporated as circular plasmids have conferred stable resistance to G418 at concentrations of 12 μg/ml, which is 4 times the concentration required to kill nontransfected amebae. Electroporation of amebae with a construct containing a frame shift at +97 base pairs into the open reading frame of neo has not (in multiple attempts) resulted in resistance to G418. These experiments demonstrate that the G418 resistance observed in amebae transfected with pTCV1&2 is due to stable expression of neo.

Location of neogene in stably transfected amebae:

The neogene has been detected by PCR and by Southern blot analysis 1 month after transfection. DNA was purified from the total population (not clones) of amebae selected with G418 after transfection. Southern blots of amebic DNA digested with NdeI (which cuts both pTCV vectors once) and probed with neo demonstrated major bands of 7.4 kB and 19 kB for pTCV1 and pTCV2-transfected amebae respectively. The 7.4 kB NdeI band is the expected size for pTCV1 remaining episomal in pTCV1-transfected amebae. The 19 kB NdeI band for pTCV2-transfected amebae is the expected size for supercoiled pTCV2 plasmid and suggests that pTCV2 is also in an episomal location in the transfected amebae.

Figure 9A:
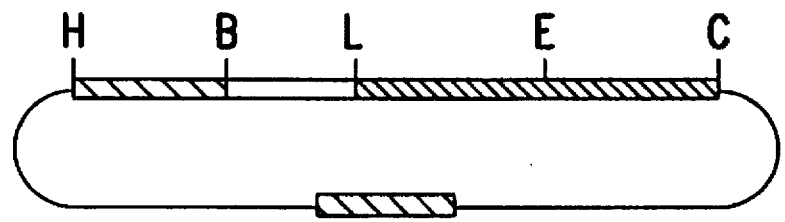
FIG. 9. Southern blot analysis of transfected *E. histolytica*. Genomic DNA from *E. histolytica* was isolated from cells growing in 75 cm² flasks as described and digested with restriction enzymes and electrophoresed on an 0.8% agarose gel. The gel was transferred to a nylon membrane and hybridized with the BamHI—SalI fragment of pTCV1 (which contains the entire coding region of the neogene) labeled by random priming. Molecular weight markers (in kilobases) are shown at the left. (A) Restriction enzyme map of pTCV1. ▨, 5' flanking region of hgl1; ■, neo gene; ■, 3' flanking region of hgl1; ▨,β=lactamase gene; H, HindIII; B, BamHI; L, SalI; E, EcoRI; C, SacI. (B) DNA digested with HindIII. Lane 1: untransfected HM-1:IMSS amebae. Lane 2: pTCV1-transfected amebae grown in G418 (6 μg/ml). Lane 3: purified pTCV1 from *E. coli* (C) Replication of pTCV1 in *E. histolytica*. DNA was digested with Sau3A in lanes 1 and 2 (a methylation-insensitive enzyme) or its isoschizomer MboI in lanes 3 and 4 (a methylation-sensitive enzyme). Lanes 1 and 3: genomic DNA from transfected *E. histolytica*. Lanes 2 and 4: purified pTCV1 from *E. coli*.
Figure 9B:
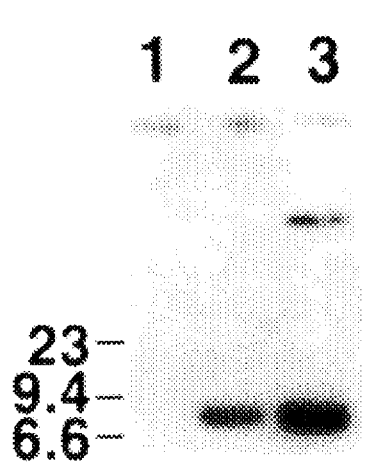
Figure 9C:
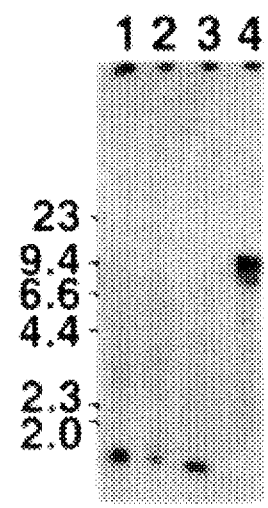

DNA was also analyzed from pTCV1-transfected amebae after digestion with restriction enzymes. On southern blots, aneo probe hybridized to a 7.2 kb HindIII fragment in pTCV1-transfected amebae. This band co-migrated with a band produced by HindIII digested pTCV1 isolated from *E. coli* (FIG. 9B). The copy number of pTCV1 from amebae growing in 6 μg/ml of G418 was estimated to be between 1–10 copies/amebae. RepliCation of pTCV1 is amebae was assayed with restriction enzyme isoschizomers that are differentially sensitive to methylation (FIG. 9C). The methylation-insensitive enzyme Sau3A cleaved pTCV1 from transfected amebae and pTCV1 from bacteria yielding bands of the same size, as shown in lanes 1 and 2. The methylation-sensitive enzyme MboI cleaved pTCV1 from transfected amebae, but was unable to cleave the pTCV1 propagated in bacteria. These data provided evidence for episomal replication of pTCV1 in transfected amebae.

Figure 10:
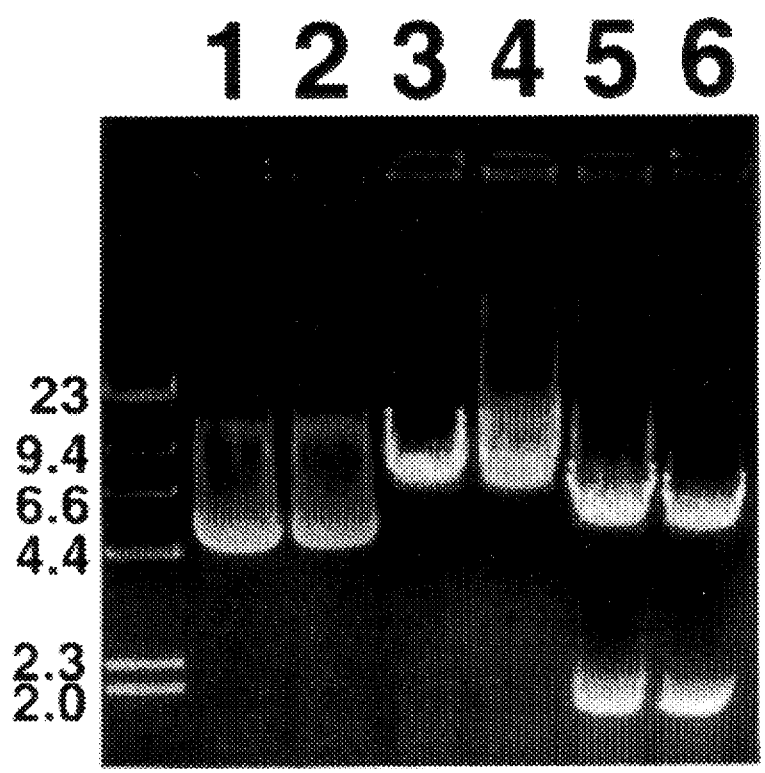
FIG. 10. Rescue of transfected pTCV1 in *E. coli*. Genomic DNA from pTCV1-transfected amebae was used to transform *E. coli*. DNA from ampicillin-resistant bacteria generated by transformation with the amebic DNA was subjected to restriction enzyme digestion, electrophoresed on an 0.8% agarose gel and visualized by ethidium bromide staining. Molecular weight markers (in kilobases) are shown at the left. Lanes 1, 3, and 5: pTCV1 in *E. coli* after passage through amebae. Lanes 2, 4 and 6: original pTCV1 plasmid from *E. coli* used to transfect *E. histolytica*. Lanes 1 and 2: uncut. Lanes 3 and 4: HindIII digested. Lanes 5 and 6: SalI, EcoRI double digested.

Further evidence of the episomal nature of pTCV1 in transfected amebae was provided by the reintroduction of pTCV1 isolated from amebae back in *E. coli* (FIG. 10). Genomic DNA from pTCV1-transfected amebae was introduced into *E. coli* by transformation, producing ampicillin-resistant bacteria. Plasmid DNA recovered from these bacteria co-migrated with the original pTCV1 plasmid used to transfect *E. histolytica* when undigested (lanes 1 and 2), HindIII digested (lanes 3 and 4), or SalI, EcoRI double digested (lanes 5 and 6). G418-resistant amebae were not obtained when the amebae were transfected with aneo gene containing a frame shift at amino acid 33, indicating that a functional neo product was required for stable transfection. To date, we have grown pTCV1-transfected amebae in the presence of G418 for several months at concentrations of up to 24 μg/ml. Stable transfection was also obtained using a construct which contained neo flanked by actin sequences. With the ability to stably transfect *E. histolytica* it will now be possible to employ a genetic approach to study of virulence in an epteric parasite. The pTCV1 vector permits the shuttling of DNA between *E. coli* and *E. histolytica* and will enable genetic complementation studies to be performed by virtue of its episomal expression.

*E. histolytica* trophozoites can be cloned in Petri dishes.

The method of Gillin & Diamond (1978), for cloning *E. histolytica* trophozoites in tubes of soft agar, was adapted to a system where the colonies can be grown in Petri dishes as follows:

Trophozoites of *E. histolytica* (strain HM-1: IMSS) were chilled on ice for 10 minutes and diluted to a concentration of $10^3$ trophozoites/mL with fresh TYI-S-33 medium (Diamond et al., 1978). A 5% (w/v) solution Bacto-agar® (Difco, Detroit, Mich., U.S.A.) TYI-S-33 medium base (prepared fresh weekly without serum, vitamin mixture or antibiotics) was autoclaved for 15 minutes and equilibrated at 55° C. in a waterbath. 30 mL of TYI-S-33 medium (containing 250 units/mL penicillin and 250 μg/mL streptomycin) were equilibrated to 42° C. for 10 minutes in 50 mL conical tubes. *E. histolytica* trophozoites/mL suspension) were added to the 30 mL of TYI-S-33 medium at 42° C. and the tubes inverted 5 times to mix. The 5% agar solution at 55° C. was added to the amoebic suspension (one tube at a time) to produce a final agar concentration of 0.3–0.8%. The final volume was adjusted to 40 mL with TYI-S-33 medium. The agar and amoebae were mixed by inverting the tube 10 times and the contents were then immediately poured into a Petri dish (plastic, $100^{33}$ 15 mm, Fisher Scientific Company, Pittsburgh, Pa., U.S.A.). The Petri dishes were placed in a −20° C. 20 freezer for 10 minutes to allow the agar to set and were then placed in a 100% anaerobic environment at 37° C. (BBL Gas-Pak® Pouch, Becton Dickinson Microbiology Systems, Cockeysville, Md., U.S.A.). The colonies were visible to the naked eye after 3 d and were easily isolated and cultured at day 5. The colony forming efficacy (number of colonies formed/number of cells inoculated) was on average 50% when 100–500 amoebae were plated (Table).

Efficiency of colony formation by *E. histolytica* on agar plates

| Amoebae/ plate | Colonies formed | | | Average | Colony forming efficiency |
|---|---|---|---|---|---|
| 100 | 40 | 52 | 50 | 47 | 47% |
| 200 | 139 | 95 | 98 | 111 | 56% |
| 500 | 272 | 252 | 223 | 249 | 50% |

The best results were obtained with amoebic cultures less than 72-hours old, freshly made agar/TYI mixture and an agar concentration of 0.55%. The colonies are easily removed from the agar the growth and analysis with a Pasteur pipette. If needed, tens of hundreds of separate neomycin resistant colonies after transfection can be isolated and analyzed.

Having now fully described the invention, it will be apparent to one of ordinary skill in the art that many changes and modifications can be made thereto without departing from the spirit or scope of the invention as set forth herein.

---

What is claimed as new and desired to be secured by Letters Patent of the United States is:

1. A method for obtaining an enteric protozoan which expresses foreign genes comprising the steps of:
    transfecting the enteric protozoan *Entamoeba histolytica* with an expression vector containing (i) at least 157 base pairs of 5' flanking DNA sequence isolated from a protein-encoding gene of the enteric protozoan *Entamoeba histolytica* which enables expression of the foreign gene in said enteric protozoan and (ii) a gene which is to be expressed operably linked to said flanking DNA sequence, and isolating a transformed enteric protozoan.

2. The method according to claim 1, wherein said transfecting is performed by electroporation.

3. The method according to claim 2, wherein said electroporation is performed in cytomix.

4. The method according to claim 2, wherein said electroporation is performed in incomplete cytomix containing DEAE-dextran.

5. The method according to claim 2, wherein said electroporation is performed at expression vector concentrations of 1–80 µg/cuvette.

6. The method according to claim 2, wherein said electroporation is conducted with a capacitance of 250 µF–960 µF.

7. The method according to claim 6, wherein said electroporation is conducted with a voltage of 500 V/cm.

8. The method according to claim 7, wherein said voltage and capacitance results in a time constant of 5–15 msec.

9. The method according to claim 8, wherein said time constant is for about 10 msec.

10. A transformed enteric protozoan isolated by the method of claim 1.

11. A method to express a foreign or altered protein in an enteric parasite comprising the steps of:
    transfecting an enteric protozoan *Entamoeba histolytica* with an expression vector containing (i) at least 157 base pairs of 5' flanking DNA sequence isolated from a protein-encoding gene of an enteric protozoan and (ii) a foreign or altered gene operably linked to said flanking DNA sequence,
    isolating a transformed enteric protozoan,
    and culturing said transformed enteric protozoan,
    wherein said foreign or altered protein is expressed.

12. The method of claim 11, wherein said 5' flanking sequence comprises at least base pairs −287 to −0 of the 5' flanking sequence isolated from a hgl1 gene of *E. histolytica*.

13. The method of claim 11, wherein said expression vector further comprises (iii) at least 0.5 kb of 3' flanking DNA sequence isolated from a protein-encoding gene of an enteric protozoa.

14. The method of claim 13, wherein said 3' flanking sequence comprises 2.3 kb of 3' flanking sequence from the hgl1 gene of *E. histolytica*.

15. A plasmid comprising (i) at least 157 base pairs of 5' flanking DNA sequence isolated from a protein-encoding gene of an enteric protozoan *Entamoeba histolytica*, which enables expression of a foreign gene in said enteric protozoan and (ii) said foreign gene operably linked to said flanking DNA sequence.

16. The plasmid of claim 15, which further comprises a selectable marker.

17. The plasmid of claim 16, wherein said selectable marker is a neomycin resistance gene.

18. The plasmid of claim 15, which further comprises a fragment of rDNA episome from an enteric protozoa.

19. The plasmid of claim 18, wherein said fragment is the dHMd or dHMe fragment or rDNA episome from *E. histolytica* shown in FIG. 5.

20. The plasmid of claim 19, which is the dHMd fragment of rDNA episome from *E. histolytica* shown in FIG. 5.

21. Plasmid pTCV1.

22. Plasmid pTCV2.

23. A transformed enteric protozoan, *Entamoeba histolytica*, containing a plamid comprising (i) at least 157 base pairs of 5' flanking DNA sequence isolated from a protein-encoding gene of *Entamoeba histolytica*, which enables expression of a foreign gene in said enteric protozoan and (ii) said foreign gene operably linked to said flanking DNA sequence.

24. The transformed enteric protozoa of claim 23, wherein said plasmid further comprises a selectable marker.

25. The transformed enteric protozoa of claim 23, wherein said plasmid is pTCV1.

26. The transformed enteric protozoa of claim 23, wherein said plasmid is pTCV2.

* * * * *